United States Patent [19]

Akagawa et al.

[11] 4,006,411
[45] Feb. 1, 1977

[54] STATIC CAPACITANCE TYPE SENSOR

[75] Inventors: Masatake Akagawa, Yachiyo; Takeshi Maki, Kawasaki, both of Japan

[73] Assignee: Asahi Kasei Kogyo Kabushiki Kaisha, Osaka, Japan

[22] Filed: Apr. 29, 1975

[21] Appl. No.: 572,897

[30] Foreign Application Priority Data

Apr. 30, 1974 Japan ............................ 49-48980

[52] U.S. Cl. ............................................ 324/61 R
[51] Int. Cl.² ...................................... G01R 27/26
[58] Field of Search ................................. 324/61 R

[56] References Cited

UNITED STATES PATENTS

| | | | |
|---|---|---|---|
| 2,950,436 | 8/1960 | Butticaz et al. | 324/61 R |
| 3,009,101 | 11/1961 | Locher | 342/61 R |
| 3,039,051 | 6/1962 | Locher | 324/61 R |
| 3,185,924 | 5/1965 | Locher | 324/61 R |
| 3,195,816 | 7/1965 | Mercer | 324/61 R X |
| 3,221,171 | 11/1965 | Locher | 324/61 R |
| 3,234,460 | 2/1966 | Baird | 324/61 R |
| 3,593,128 | 7/1971 | Perry | 324/61 R |
| 3,757,211 | 9/1973 | Goto | 324/61 R |

*Primary Examiner*—Stanley T. Krawczewicz
*Attorney, Agent, or Firm*—Armstrong, Nikaido & Wegner

[57] ABSTRACT

A static capacitance type yarn denier sensing arrangement is provided which includes a high frequency current source and a sensing condenser which has a pair of opposing electrodes electrically coupled with both sides of the h.f. current source and representing a passage for passing a yarn under measurement. The high frequency current from said current source is subject to amplitude modulation in response to instant denier variation of the yarn. The arrangement further includes a half wave voltage doubler rectifier circuit which is electrically connected with the sensing condenser acting as an input condenser to be included therein and an amplifier adapted for amplifying the output from the rectifier circuit.

8 Claims, 16 Drawing Figures

STATIC CAPACITANCE TYPE SENSOR

BACKGROUND OF THE INVENTION

This invention relates to improvements in and relating to an arrangement for precise and continuous measurement of yarn thickness and mass while the yarn is running by use of a static capacitance type sensor.

It is commonly known to use a static capacitance type sensor having a pair of opposing electrodes defining a gap passage for the yarn under measurement by and between these electrodes. In order to control the spinning conditions on location where at least several thousand yarns are being manufactured, each spinning unit must be provided with such a sensor. This kind of sensor must have outer dimensions which are as small as possible without sacrificing its precise operational performance.

According to our experimental study, future dyeing capability of the yarn can be estimated at the manufacture or winding or packaging stage of the process and in advance of the practical dyeing of the yarn, by precise and fine measurement of denier variations thereof taken along its whole length. For such purpose, the above mentioned kind of sensor must be utilized.

In order to realize a smaller possible sensor of the static capacitance type with superior operation performance, it is necessary to shorten the length of the electrode as much as possible when seen in the running direction of the yarn; ideally to a point. If the yarn denier measurement could be carried out continuously at a point or in the differential way so to speak, the measured result would be best. But, in practice, such measurement mode has only an ideal significance.

In order to precisely take out the electrical output from the statical capacitance sensor, a resonance circuit must have been coupled with the electrode pair due to the extremely small variations of the capacitance measured in correspondence to those of the yarn denier.

With use of the resonance circuit for an extended time period, appreciable variation in the temperature characteristic of each of the circuit components will be encountered, resulting in the corresponding shift of the resonance point. A usable time period of such a measuring arrangement having a static capacitance sensor and resonance circuit may be in the order of 2 - 3 minutes if the precise measurement of fine and smaller yarn denier variations are to be performed in a satisfactory manner. In order to avoid such adverse effect, the condenser capacitance of the sensor must have a reasonably large value, such as, preferably, 10 pF or so. The corresponding electrode length may be in the order of 10 cm.

If the impedance drop method is employed in place of the resonance system, the sensitivity will drop considerably by virtue of the nonemployment of the resonance amplification. In this case, therefore, the amplifier used for the amplification of output signal from the sensor must have a considerably large amplifying factor which results in a considerable rise in the amplifier cost.

SUMMARY OF THE INVENTION

The main object of the present invention is to provide an improved sensor unit operable at high efficiency and close preciseness adapted for fine and accurate measurement of yarn denier variations.

For attaining this object, a voltage doubler rectifier is coupled with the sensor electrodes in the circuit wherein the sensor condenser is used as the input condenser of the voltage doubler rectifier. Otherwise, if the sensing condenser is arranged to act as per se and in addition to the input condenser, a voltage division will occur by and between these condensers, thus reducing considerably the operating efficiency of the circuit.

This and further objects, features and advantages of the invention will become more apparent as the description proceeds with reference to the accompanying drawings showing several preferred embodiments of the invention in comparison with two comparative conventional circuits.

BRIEF DESCRIPTION OF THE DRAWINGS

In the drawings:

FIG. 10, (A) - (D)

DETAILED DESCRIPTION OF THE PREFERRED EMBODIMENTS

In the following, the invention will be described with reference to the accompanying drawings.

Figure 1:
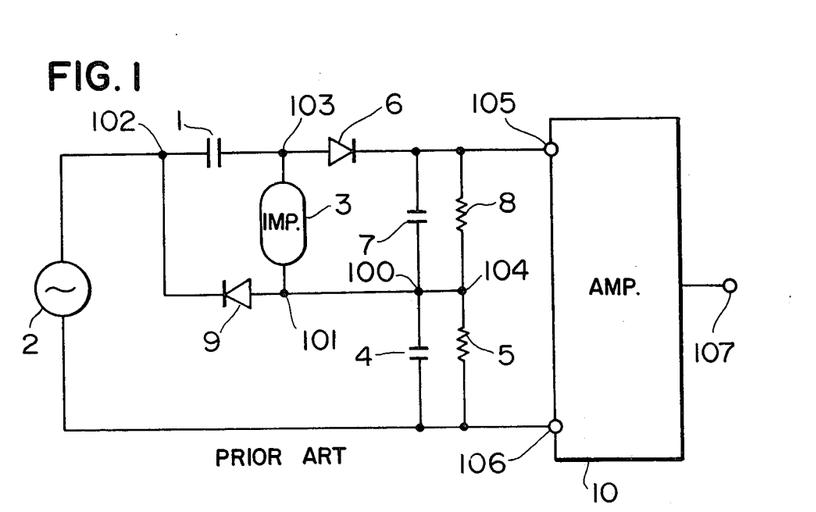
FIGS. 1 and 2 are schematic connection diagrams of two comparative conventional arrangements.

In FIG. 1 showing a conventional unit in its circuitry, numeral 1 denotes a detecting condenser having one electrode thereof electrically connected with one side of a high frequency current source 2, while the opposite electrode is connected through an impedance element 3 and a parallel combination of condenser 4 and resistor 5 to the opposite side of the source 2. One side of impedance element 3 is electrically connected through a diode 6 to one side of the parallel combination of condenser 7 and resistor 8, while junction point 100 between the condensers 4 and 7 is connected through junction point 101, diode 9 and junction point 102 to one side of the high frequency current source 2. The latter junction point 102 is connected through condenser 1 to a further junction point 103 which is at the common point between impedance element 3 and diode 6. A junction point 104 is positioned between the resistors 5 and 8 and is connected to the first-mentioned junction point 100.

As the impedance element 3, a coil is generally used and arranged to provide a series resonator relative to the frequency of the source 2 in cooperation with the sensing condenser 1.

The voltage appearing across impedance element 3 is rectified through the diode 6 and the thus rectified current is smoothed by the combination of condenser 7 and resistor 8. The initial voltage across the diode 9 is cancelled out by the smoothed voltage by means of condenser 4 and resistor 5. Thus, the input terminals 105, 106 of an operational amplifier 10, connected across the series-connection of resistors 5 and 8, will be zero.

When a yarn, not shown, is passed through the sensing condenser 1, the static capacitance thereof is varied and the circuit deviates from the series-resonant position and a variable input will appear at the input terminals of amplifier 10. The variable capacitance change at the condenser 1 caused by the denier variations of the running yarn is a small value. Thus, the condenser 1 is designed to have a small capacitance value to enable detection of such a change, while the frequency at the source 2 is designed to have a rather high value, such as, for instance, 10 − 100 MHz.

Since the combination of condenser 1, and coil 3 is kept in series-resonance condition, stray capacitance may frequently appear between coil 3 and the case, not shown, of the sensor unit which capacitance naturally provides an adverse effect to the unit. To eliminate the adverse effect, the diode 6 represents generally a high interrupting resistance which resulte in an inferior sensing capability for of the unit.

A resistor may be used as the impedance element 3 in place of the coil in the above known arrangement. In this case, the resonance phenomenon will disappear and the output to be supplied to the amplifier will become very small. Therefore, the gain at the amplifier 10 must be appreciably enlarged with a correspondingly increased noise level.

Figure 2:
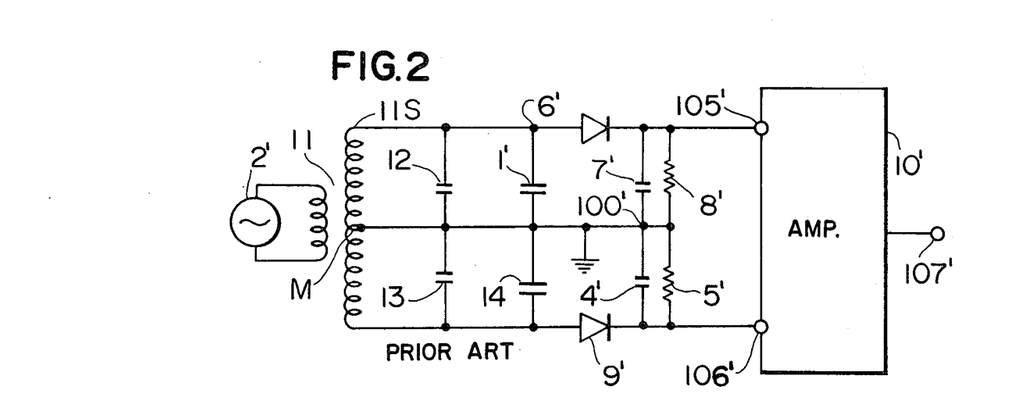

A modification from the foregoing known arrangement is shown at FIG. 2. In this modification, the output from the source 2 is supplied to primary winding of a phase-reversing transformer 11, a midpoint M of the secondary winding 11s and one end thereof, being connected to a parallel combination of the sensing condenser 1' and a further condenser 12, so as to provide a parallel resonance circuit by cooperation with the secondary winding. In the similar way, a parallel combination of condensers 13 and 14 is inserted between midpoint M and the opposite end of the secondary winding, so as to provide another a parallel resonance circuit. Condensers 12 and 13 have equal capacitances and similarly, condensers 1' and 14 have equal capacitances. The resonance voltages of these both resonance circuits have been designed to be equal to each other.

The ends of the secondary winding are connected through diodes 6', 9' to respective capacitor-resistor parallel circuits 4', 5' and 7', 8', the smoothed outputs therefrom being kept in blance with to each other and thus, the input at the terminals 105', 106' being zero. However, when a yarn, not shown, is passed through the sensing condenser 1', the resonance condition of the upper resonance circuit including the sensing condenser 1' is altered and a variable input corresponding to the yarn denier alteration is supplied to the amplifier 10' through its input terminals 105', 106'.

In the sensor arrangement shown in FIG. 2, it will be seen that outside influence acts equally upon the both resonance circuits included therein and the effects being cancelled out by each other.

If, however, it is desired to use a sealed casing, not shown, with the sensor arrangement shown, substantial difficulty will occur in designing the casing, to provide equal effects in both resonance circuits. A perfect pre-balanced condition between these resonance circuits is highly difficult to realize. When used for a long time period, the resonance point will shift by unavoidable aging of the constituent parts, resulting in the possibility of an unbalanced condition. As a counter measure in such a case, an outside adjuster means must be provided which invites a substantial complexity of the whole arrangement and an increased manufacturing cost thereof.

Figure 3:
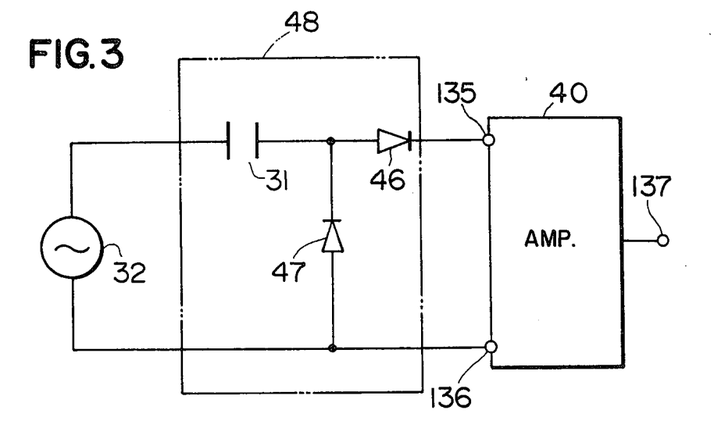
FIGS. 3 - 7 are schemmatic diagrams showing several different embodiments according to this invention.

In the first embodiment of the present invention shown in FIG. 3, the static capacitance type sensor is shown at 31, one electrode thereof being connected to one side of high frequency source 32 which is similar to that shown at 2 or 2' in the previously described embodiments. The opposite electrode of the said sensor or condenser is connected to the anode of a diode 46 as well as the cathode of a further diode 47. The cathode of diode 46 is connected to input 135 of an operational amplifier 40 similar to that shown to that denoted 10 or 10' in the previously described embodiments and having an output terminal 137 as at 107 or 107' in the foregoing.

The anode of diode 47 is connected to the opposite side of source 32 as well as common terminal 136 of the amplifier 40. In this arrangement, the combination of condenser 31, diodes 46 and 47 constitutes a half wave voltage doubler rectifier 48 the input condenser of which is the sensing condenser 31.

With the half waves of the source current from 32 which make the anode of diode 47 to be positive, the condenser 31 is charged, with the right hand electrode kept positive.

With the arrival of succeeding half waves of the opposite polarity, the condenser electrode at 31, directing toward source 32, becomes positive, and the source voltage at this moment and the voltage at the said condenser act in series to each other and are rectified at 46. Therefore, the output voltage is doubled in comparison with that obtained with the single effective condenser arrangement.

When a yarn is passed through the passage formed by and between the electrodes at 31, the static capacitance value thereat will be subjected to alteration in accordance with variations of yarn denier. Therefore, the rectified output does vary therewith, and a corresponding and amplified output voltage may be taken out from the output terminal 137.

Noise calcellation as was referred to in connection with FIG. 2 may equally be applied to the embodiment shown at FIG. 3.

Figure 4:
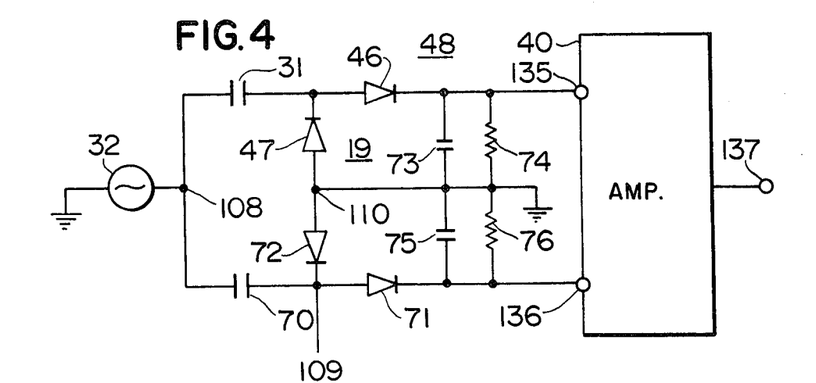

Such a modified embodiment is shown at FIG. 4. The same reference numerals as those employed in FIG. 3 represent similar or equal corresponding circuit constituents. More specifically, this applies to those denoted 31, 32, 46 − 48, 135, 136 and 137. In this arrangement, a comparative condenser 70 is provided. One electrode of this condenser is connected with a junction 108 arranged between sensor condenser 31 and source 32, while the opposite electrode is connected to a junction 109 between condensers 71 and 72. The anode of diode 72 is connected through junction 110 the anode of diode 47. The cathode of diode 46 is grounded through a parallel combination of condenser 73 and resistor 74. In a similar way, the cathode of diode 71 is grounded through a parallel arrangement of smoothing condenser 75 and resistor 76.

The cathodes of diodes 46 and 71 are connected to input terminals 135 and 136 to amplifier 40, respectively. The opposite side of source 32 is grounded as shown.

With no yarn placed on the sensing condenser 31, the inputs to amplifier are balanced and the d. c. output from 137 is null.

With insertion of a yarn in the condenser 31 the static capacitance of the condenser will be subjected to variation and thus the voltage charged in this condenser from source 32 and the voltage charged in the condenser 70 differ from each other and a d. c. voltage corresponding to this voltage difference will be supplied to the amplifier 40 through its input terminals 135; 136, to be amplified.

The thus amplified output appearing at the output terminal 137, FIG. 4, corresponds to the instant dielectric mass of the yarn under measurement.

Figure 5:
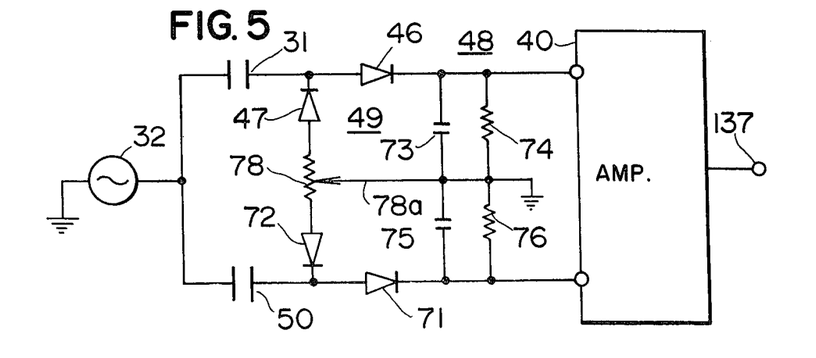
Figure 6:
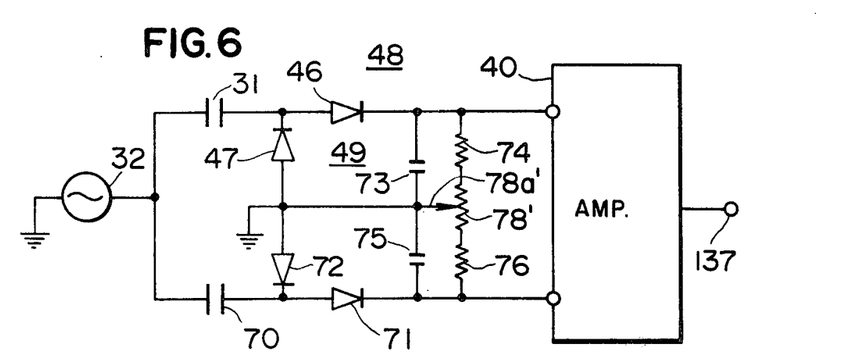

In order to adjust an unbalance between condensers 31 and 70 and at the d. c. side, any one of the two different counter measures may be employed, as shown in FIGS. 5 and 6.

In the first modification shown at FIG. 5, the junction point 110 has a variable resistor 78 and the adjustable top thereof 78a is grounded.

In the second modification shown at FIG. 6, a variable resistor 78' is inserted between the resistors 74 and 76 and the adjustable top thereof 78a' is grounded.

Figure 7:
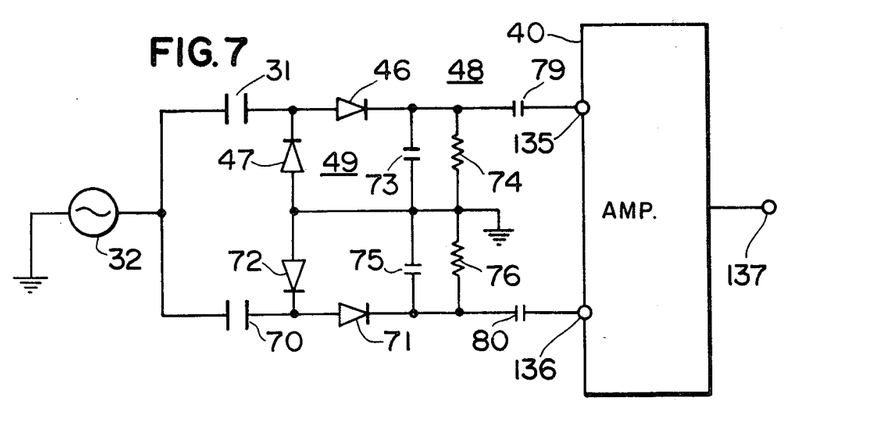

In order to take out only denier- or mass deviation of the yarn under measurement, a still further modified embodiment shown in FIG. 7 may be employed. In this case, respective rectified outputs from diodes 46 and 71 are supplied through respective condensers 79 and 80 to input terminals 135 and 136 of the amplifier 40, respectively. In this case, occasional unbalance between the d. c. voltage caused by the unbalance between the capacitances of condensers 31 and 70 has no influence on the output at 137 so that no correction means need be provided. It will be clear from the foregoing disclosure that the conventionally used resonance circuit, and in particular the coil means included therein may be dispensed with according to the principle of the present invention for a yarn denier sensor unit for sensing out fine and minor capacitance variations caused by the yarn when being run through a sensor condenser. Occasionally necessary adjustment of adjusting means employable in the inventive unit can be highly simplified when compared with the conventional adjusting operation of a resonator employed in the conventional technique. Outside adverse effects can also be minimized by virtue of elimination of the conventional resonator circuit. The unit can be used for a long time period without adjustment and further, without aging variations in the characteristic performance of the included circuit elements.

The doubled voltage rectifier may be replaced with equal result by 3- or 4-fold voltage rectifier.

Figure 8:
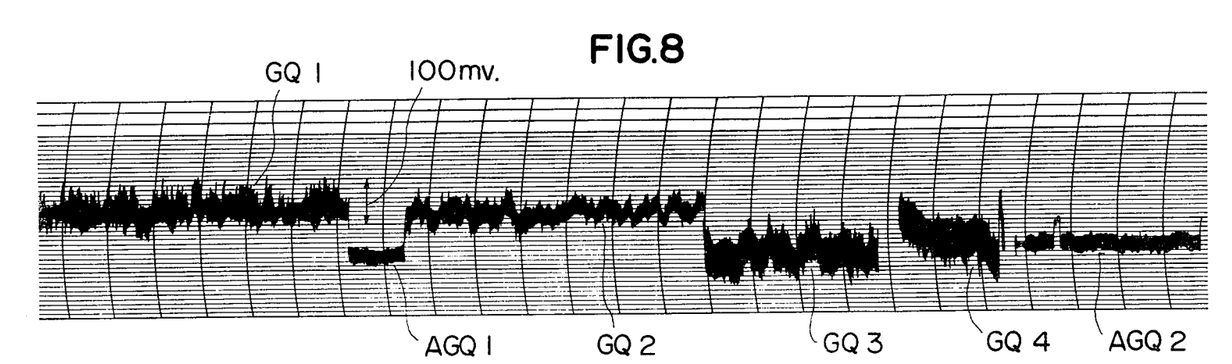
FIG. 8 is a signal chart showing noises of the sensor.

FIG. 8 represents a comparative and combined chart showing relative noises appearing at respective output terminals 107 and 137 shown in FIGS. 1 and 7. In this case, the yarn has not yet been placed in the respective sensor 1 or 31 for showing the desired noise output. In FIG. 8, GQ1 – GQ4 represents three representative noise models measured practically on or from three known sensors corresponding to that shown at 1. In the similar way AGQ1 and AGQ2 represent two modes of noise output practically measured at 137 shown in FIG. 7. The arrangements shown in FIGS. 1 and 7 have been so designed and constructed to obtain 8-volt output at each of the said output terminals 107 and 137 when a 50-denier polyester yarn has been placed on the sensor and kept stationary without running.

When compared, as an example, between GQ1 and AGQ1, the nose level is 0.1 and 0.03 volt, respectively, the design signal level being 8.00 volts, respectively. Thus, the SN-ratio will be 80 : 1 and 800 : 3, respectively and the merits and improved results are self-explanatory.

Figure 9:
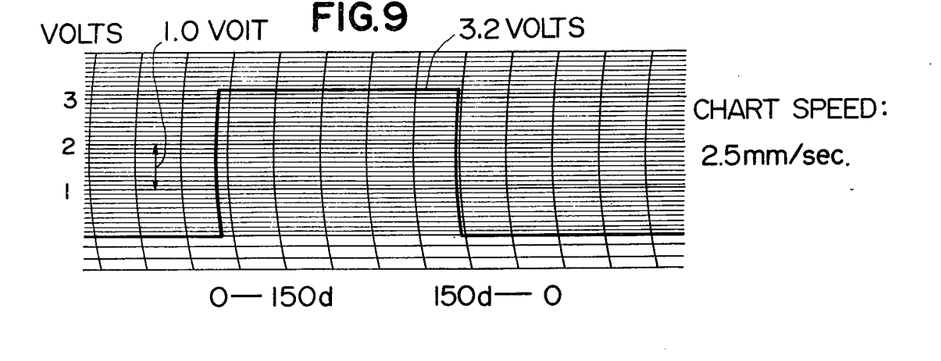
FIG. 9 is a static signal chart showing an output of the sensor when a yarn is placed in the sensor.

An example of static signal output measured at each of the output terminals, being commonly denoted 137, appearing at FIGS. 4, 5 and 6, respectively is shown at FIG. 9, wherein the yarn, having a 150 denier was placed in each of the sensors. The voltage range extends from 0 to 3.2 volts. These values were measured at a chart speed of 2.5 mm per second. The yarn was of 150d/32 fils. acrylonitrile fibers.

Figure 10:
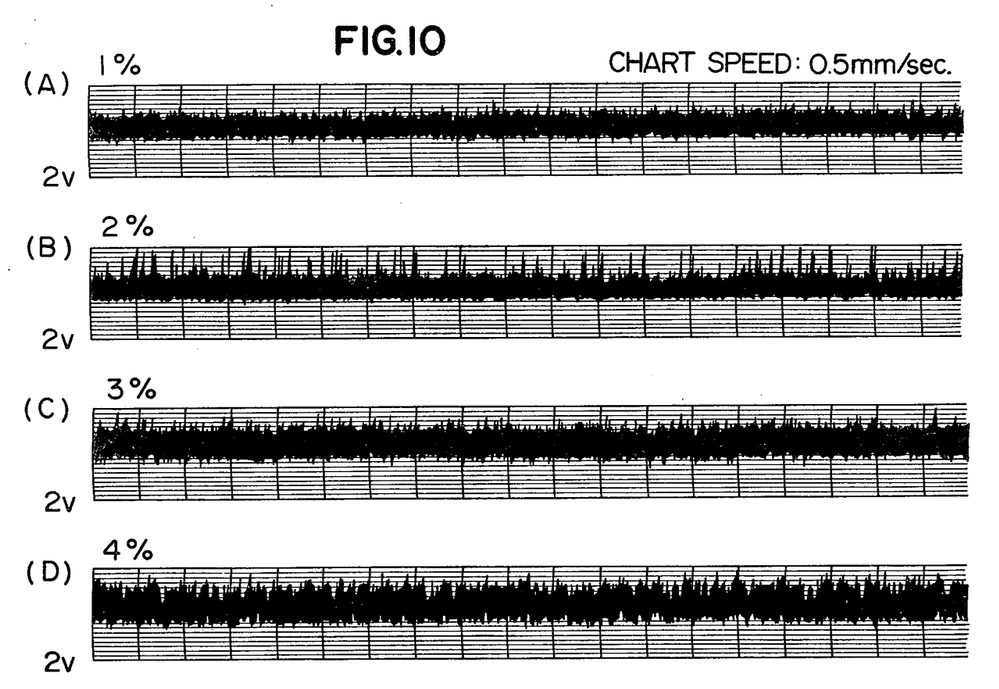

Several signal charts shown at (A) – (D) in FIG. 10 are examples of the output appearing at each of the output terminals 137 shown at FIGS. 4 – 6. In each of these cases, the yarn of nominal diameter, 150 denier plus 1, 2, 3 and 4% deviation in the mean, was passed through the sensor. As seen, with larger deviation in the mean, the signal represents mean level and broader signal range. The yarn travel speed was 120 meters per minute.

Figure 11:
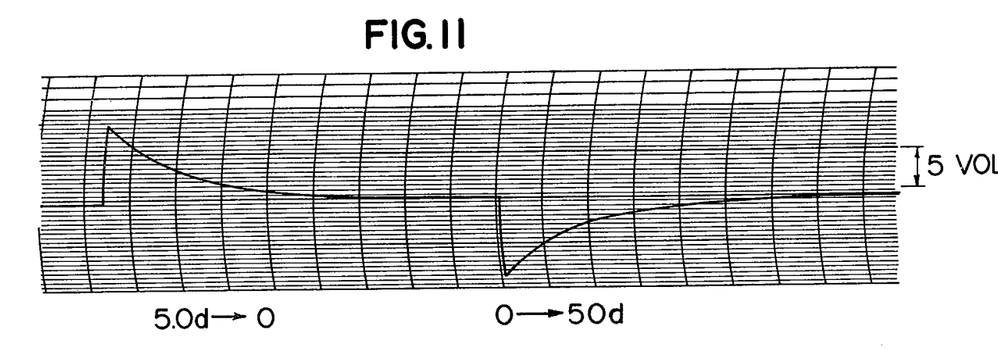
FIGS. 11 - 12 show several signal charts for the illustration of the unit according to the invention.

In FIG. 11, a static signal chart is shown which was obtained at the terminal 137 of the arrangement shown at FIG. 7 by on- and off condition of the sensor with the yarn of 50d/24 fil. polyester multifilament. Max. output voltage was 8.0 volts as shown.

Figure 12:
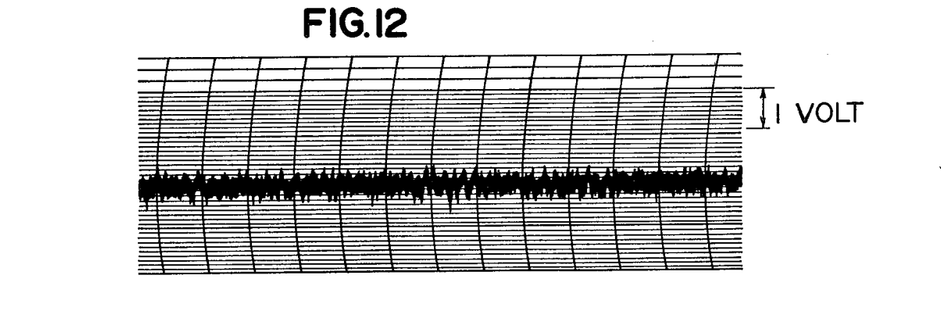

In FIG. 12, an output signal chart with use of the arrangement shown in FIG. 7 is illustrated. The yarn was of the same kind as that described above with reference to FIG. 11. The yarn travel speed was 900 meters per minute, while the chart speed was 0.5 mm per second.

Figure 13:
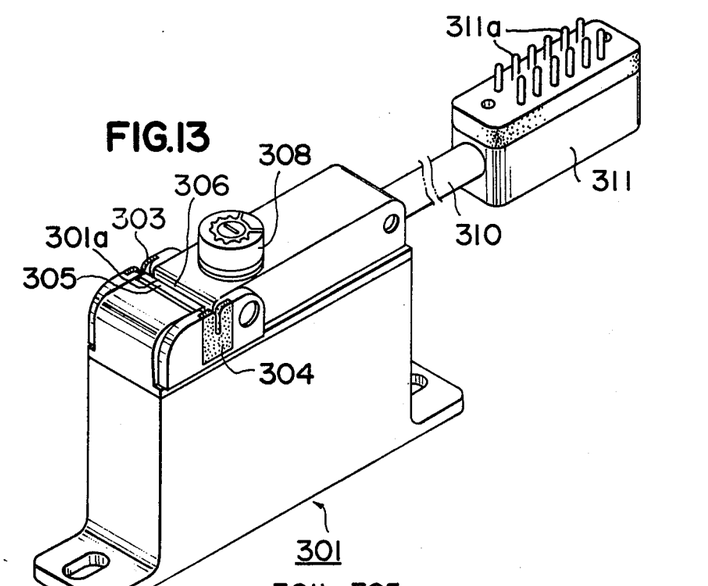
FIG. 13 is a perspective view of the sensor unit employed in the present invention.

A specific configuration of the sensor usable in each of the arrangements shown in FIGS. 5 – 6 is illustrated in FIG. 13 generally at 301.

Numeral 301a represents a yarn passage gap which is formed between a pair of static capacitance electrodes 305 and 306. Numerals 303 and 304 represent respective stationary yarn guides defining the initial end and the terminating end of the yarn passage.

Numeral 301b represents a comparative gap constituting a noise-cancellation condenser as shown commonly at 70 in FIGS. 4 – 7 by cooperation with the neighboring electrode at 307 and the detecting electrodes 305; 306, constituting the sensing condenser 31.

Figure 14:
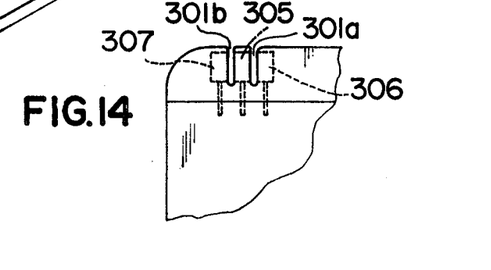
FIG. 14 is a partial and schematic view of the sensor shown in FIG. 13.

Numerals 305; 306 and 307 shown in FIG. 14 represents three physically parallel electrodes which in combination define two parallel electrode gaps 301a and 301b. The middle electrode 305 thus constitutes a common electrode for the formation of said gaps 301a and 301b.

Figure 15:
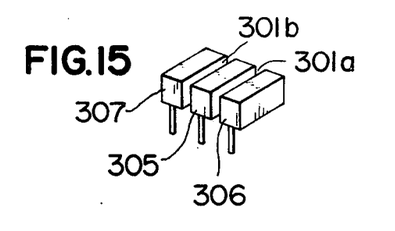
FIG. 15 is a schematic perspective view of the electrodes arrangement of the sensor.

In FIG. 15, these three electrodes 305; 306 and 307 are shown in their schematic perspective view. Each of the electrode gaps 301a and 301b has a dimension of 0.6 – 1.0 mm. The length of the electrode is approximately, while the width is approximately 5 mm. Numeral 308 appearing in FIG. 13 represents the head of an adjusting screw adapted for adjusting the variable resister 78 or 78' shown in FIGS. 5 or 6. Numeral 310 represents a group of connecting cables leading to plugs 311a projecting from a connector unit 311.

Figure 16:
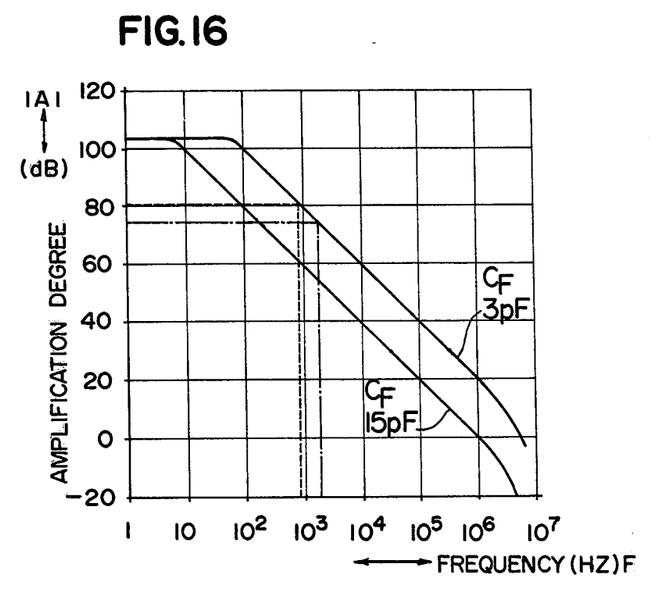
FIG. 16 is a characteristic performance chart of an amplifier employed in the present invention.

As the operational amplifier 40 shown in FIGS. 3 – 7, Type model LM 301A manufactured and sold by National Semi-Conductor Corporation (U.S.A.) may be used for example, having operational characteristics illustrated on the chart shown at FIG. 16 wherein the X-axis represents frequency while the Y-axis represents the degree of amplification.

In the shown example, the phase correction condenser, $C_F$, has a capacitance value of 3 pF.

When comparing the conventional arrangement of FIG. 1 with the inventive arrangement of FIGS. 4 – 7, the dotted line in FIG. 16 represents conventional results, while the chain line illustrates the results of the inventive arrangement. Therefore, it will be seen that the degree of amplification in the inventive arrangement amounts to only about ½ of the conventional value while the frequency characteristic of the invention represents about a doubled value of the conventional for obtaining equal output performance.

Now turning back to FIG. 4, several circuit components data are shown only by way of example.

| | |
|---|---|
| sensing condenser 31 : | 0.5 pF; |
| silicon diodes 47; 76; 72; 71 : | Model 1S 21 35, of Nippon Electric Co., Tokyo; |
| resistors 74; 76 : | 20 kilo ohms; |
| condensers 73; 75 : | 2,000 pF; |
| h.f. source voltage at 32 : | peak-to-peak 40 – 60 volts; 20 MHz. |

Finally, a table is shown for demonstrating the doubled voltage output characteristics as measured at the input to the operation amplifier of the inventive arrangement. As the yarn material, polyester was used.

| OSC (p-p") Yarn denier | 40 ᵛ | 50 | 60 |
|---|---|---|---|
| 30 d | 0.7 | 1.2 | 1.7 |
| 50 d | 1.1 | 1.8 | 2.4 |
| 75 d | 1.8 | 2.6 | 3.4 |
| 100 d | 2.4 | 3.8 | 5.0 |
| 150 d | 3.3 | 5.3 | 7.2 |

Although not appearing, the sensor 301 in its broader sense and shown in FIG. 13 includes therein the voltage doubler rectifier circuit, the comparison circuit and the amplifier, so as to provide a compact unit in a single package. One of connector pins 311a may constitute said terminal 137. Other pins 311a may act as high frequency source terminals, and other source and shielding terminals for the amplifier.

THE EMBODIMENTS OF THE INVENTION IN WHICH AN EXCLUSIVE PROPERTY OR PRIVILEGE IS CLAIMED ARE AS FOLLOWS:

1. A static capacitance type yarn denier sensing circuit said circuit comprising:
   a. a high frequency current source;
   b. sensing condenser means comprising a pair of opposed electrodes with a first gap therebetween, said electrodes being connected to said current source, wherein the yarn being sensed is passed through said first gap such that the voltage across said sensing condenser means is modulated as a function of the variations in the yarn denier;
   c. a reference condenser means comprising one electrode of said pair of electrodes and a third electrode opposed to said one electrode with a second gap therebetween, wherein said second gap is the same size as said first gap;
   d. first means coupled to said sensing condenser means for forming a first voltage doubler circuit therewith wherein the voltage across said sensing condenser means is doubled;
   e. second means coupled to said reference condenser means for forming a second voltage doubler circuit therewith, wherein the voltage across said reference condenser means is doubled and is in phase with the voltage produced by said first voltage doubler circuit; and
   f. amplifier means coupled to said first and second voltage doubler circuits for producing an output equal to the difference between the outputs of said first and second voltage doubler circuits.

2. A static capacitance type yarn denier sensing circuit as set forth in claim 1, wherein said first means comprises a first diode having its anode coupled to said sensing condenser means and its cathode coupled to said amplifier means, and a second diode having its anode coupled to ground and its cathode coupled to the junction of said first diode and said sensing condenser means, and wherein said second means comprises a third diode having its anode coupled to said reference condenser means and its cathode coupled to said amplifier means and a fourth diode having its anode coupled to ground and its cathode coupled to the junction between said reference condenser means and said third diode means.

3. A static capacitance type yarn denier sensing circuit as set forth in claim 2, including equalizer means coupled to said first and second voltage doubler circuits for equalizing the outputs therefrom when the yarn denier is a constant.

4. A static capacitance type yarn denier sensing circuit as set forth in claim 3, wherein said equalizer means comprises variable resistance means.

5. A static capacitance type yarn denier sensing circuit as set forth in claim 4, wherein the cathodes of said second and fourth diodes are coupled to ground through said variable resistance means.

6. A static capacitance circuit as set forth in claim 3, including filter means coupled to the output of said first and second voltage doubler circuits for smoothing the output therefrom.

7. A static capacitance type yarn denier sensing circuit as set forth in 1, including equalizer means coupled to said first and second voltage doubler circuits for equalizing the outputs therefrom when the yarn denier is a constant.

8. A static capacitance type yarn denier sensing circuit as set forth in claim 1, including filter means coupled to said first and second voltage doubler circuits for smoothing the output therefrom.

* * * * *